United States Patent
Wu

(10) Patent No.: US 9,567,593 B2
(45) Date of Patent: Feb. 14, 2017

(54) METHOD FOR DIRECTIONAL CLONING

(71) Applicant: SiDanSai Biotechnology CO., LTD, Shanghai (CN)

(72) Inventor: Zhao Wu, Shanghai (CN)

(73) Assignee: Innovative Cellular Therapeutics CO., LTD., Shanghai (CN)

( * ) Notice: Subject to any disclaimer, the term of this patent is extended or adjusted under 35 U.S.C. 154(b) by 99 days.

(21) Appl. No.: 14/538,627

(22) Filed: Nov. 11, 2014

(65) Prior Publication Data

US 2016/0108408 A1 Apr. 21, 2016

Related U.S. Application Data

(63) Continuation of application No. PCT/CN2014/088800, filed on Oct. 17, 2014.

(51) Int. Cl.
*C12N 15/66* (2006.01)
*C12N 15/64* (2006.01)

(52) U.S. Cl.
CPC .............. *C12N 15/66* (2013.01); *C12N 15/64* (2013.01)

(58) Field of Classification Search
None
See application file for complete search history.

(56) References Cited

U.S. PATENT DOCUMENTS

| 4,994,368 | A | * | 2/1991 | Goodman | C12Q 1/6813 435/6.1 |
| 5,969,121 | A | * | 10/1999 | Allen | C12N 9/18 435/19 |
| 2003/0215854 | A1 | * | 11/2003 | Clausen | C12Q 1/44 435/6.16 |
| 2010/0291633 | A1 | * | 11/2010 | Selmer et al. | 435/91.1 |
| 2011/0244521 | A1 | * | 10/2011 | Nagai et al. | 435/91.2 |
| 2012/0196294 | A1 | * | 8/2012 | Chen | C12Q 1/6804 435/6.12 |

OTHER PUBLICATIONS

Galloway et al., Rapid cloning for protein crystallography using type IIs restriction enzymes; Crystal Growth and Design; vol. 13, pp. 2833-2839, 2013.*
Schmidt et al., High resolution insertion-site analysis by linear amplification-mediated PCR (LAM-PCR); Nature Methods, vol. 4, No. 12, pp. 1051-1057.*

* cited by examiner

*Primary Examiner* — Addison D Ault
(74) *Attorney, Agent, or Firm* — Tian IP & Technology, LLC.

(57) ABSTRACT

Described herein are techniques for directional cloning an insert DNA segments into a target vector. The techniques mix the target vector, the insert DNA segment, a restriction enzyme, and a DNA ligase to generate a recombinant DNA molecule.

6 Claims, 2 Drawing Sheets

SEQUENCE LISTING

<160> NUMBER OF SEQ ID NOS: 4

<210> SEQ ID NO 1
<211> LENGTH: 731
<212> TYPE: DNA
<213> ORGANISM: Artificial Sequence
<220> FEATURE:
<223> OTHER INFORMATION: Synthesized

<400> SEQUENCE: 1

```
ctgacgccac catggtgagc aagggcgagg agctgttcac cggggtggtg cccatcctgg      60
tcgagctgga cggcgacgta aacggccaca agttcagcgt gtccggcgag ggcgagggcg     120
atgccaccta cggcaagctg accctgaagt tcatctgcac caccggcaag ctgcccgtgc     180
cctggcccac cctcgtgacc accctgacct acggcgtgca gtgcttcagc cgctaccccg     240
accacatgaa gcagcacgac ttcttcaagt ccgccatgcc cgaaggctac gtccaggagc     300
gcaccatctt cttcaaggac gacggcaact acaagacccg cgccgaggtg aagttcgagg     360
gcgacaccct ggtgaaccgc atcgagctga agggcatcga cttcaaggag gacggcaaca     420
tcctggggca agctggagta caactacaac agccacaa cgtctatatc atggccgaca     480
agcagaagaa cggcatcaag gtgaacttca agatccgcca caacatcgag gacggcagcg     540
tgcagctcgc cgaccactac cagcagaaca ccccatcgg cgacggcccc gtgctgctgc     600
```

```
ccgacaacca ctacctgagc acccagtccg ccctgagcaa agaccccaac gagaagcgcg      660
atcacatggt cctgctggag ttcgtgaccg ccgccgggat cactctcggc atggacgagc      720
tgtacaagta a                                                          731

<210> SEQ ID NO 2
<211> LENGTH: 11
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (7)..(11)
<223> OTHER INFORMATION: n is a, c, g, or t

<400> SEQUENCE: 2
ggtctcnnnn n                                                           11

<210> SEQ ID NO 3
<211> LENGTH: 34
<212> TYPE: DNA
<213> ORGANISM: Artificial Sequence
<220> FEATURE:
<223> OTHER INFORMATION: Synthesized

<400> SEQUENCE: 3 gggggtctc ttgacgccac catggtgagc aagg                                   34

<210> SEQ ID NO 4
<211> LENGTH: 51
<212> TYPE: DNA
<213> ORGANISM: Artificial Sequence
<220> FEATURE:
<223> OTHER INFORMATION: Synthesized

<400> SEQUENCE: 4
gccgggtctc ggagttggtc tcggagttta cttgtacagc tcgtccatgc c               51
```

METHOD FOR DIRECTIONAL CLONING

CROSS REFERENCE TO RELATED APPLICATIONS

This application is a continuation of International application number PCT/CN2014/088800, filed on 31 Oct. 2014. The entirety of the aforementioned application is hereby incorporated by reference

SEQUENCE LISTING

The Sequence Listing associated with this application is provided in text format in lieu of a paper copy, and is hereby incorporated by reference into the specification. The name of the text file containing the Sequence Listing is Sequence_listing_SDS1_0004PCT.txt. The text file is about 27 KB, was created on Sep. 15, 2014.

TECHNICAL FIELD

This disclosure relates to recombinant technologies. More specifically, the disclosure relates to methods for directional cloning.

BACKGROUND

Molecular cloning is a process used to create recombinant DNA molecules. Components for formation of recombinant DNA include a cloning vector, a small DNA segment, multiple enzymes, and living cells. The cloning vector is a DNA molecule that replicates within the living cells. The small DNA segment contains a gene to be cloned. During the cloning process, the gene may be combined with the vector using various methods to form the recombinant DNA molecules. The recombinant DNA molecules are then transformed into the living cells, which are then screened and duplicated. However, conventional techniques for molecular cloning involve multiple processes under various conditions. Therefore, there is a need for a simple, efficient, inexpensive method of molecular cloning of a DNA segment into a target molecule.

SUMMARY

Described herein are methods for directional cloning of an insert DNA segment into a vector. The various embodiments including providing a target vector and an insert Deoxyribonucleic acid (DNA) segment. The target vector and the insert DNA segment may be mixed with an amount of a restriction enzyme, and an amount of a DNA ligase in a container to cleave the target vector at a first temperature and to ligate at least one portion of the insert DNA segment to the target vector at a second temperature. In some embodiments, the first temperature is the same or substantially the same as the second temperature.

In some embodiments, the insert DNA segment to the target vector may be ligated to generate a recombinant DNA molecule including at least one portion of the target vector and the at least one portion of the insert DNA segment. In these instances, the recombinant DNA is an expression vector. In some embodiments, the insert DNA segment may include the at least one portion of the insert DNA segment and DNA sequences including recognition sites of the restriction enzyme. In some embodiments, the target vector may include recognition sites of the restriction enzyme (e.g., a type II restriction enzyme).

In some embodiments, molecules of the target vector in the container substantially are closed circular plasmids when the target vector, the insert DNA segment, the amount of the restriction enzyme, the amount of the DNA ligase are mixed. In some embodiments, the target vector, the insert DNA segment, the amount of the restriction enzyme, and the amount of a DNA ligase may be mixed in a single container for a predetermined time period. For example, the predetermined time period may include a time period of from about 1 minutes to 20 minutes.

In some embodiments, the restriction enzyme may include a type II restriction enzyme. In these instances, the type II restriction enzyme may include at least one of BsaI, BbsI, BsmBI, Alw26I or LguI. In some embodiments, the DNA ligase may include at least one of T4 DNA ligase or *E. coli* DNA ligase.

In some embodiments, the Insert DNA segment may include a polymerase chain reaction (PCR) product. In some embodiments, the first temperature and/or the second temperature is a predetermined temperature. For example, the predetermined temperature may range from about 16° C. to about 37° C.

This Summary is provided to introduce a selection of concepts in a simplified form that are further described below in the Detailed Description. This Summary is not intended to identify all key features or essential features of the claimed subject matter, nor is it intended to be used to limit the scope of the claimed subject matter.

BRIEF DESCRIPTION OF THE DRAWINGS

The detailed description is described with reference to the accompanying figures.

DETAILED DESCRIPTION

Definition

Figure 1:
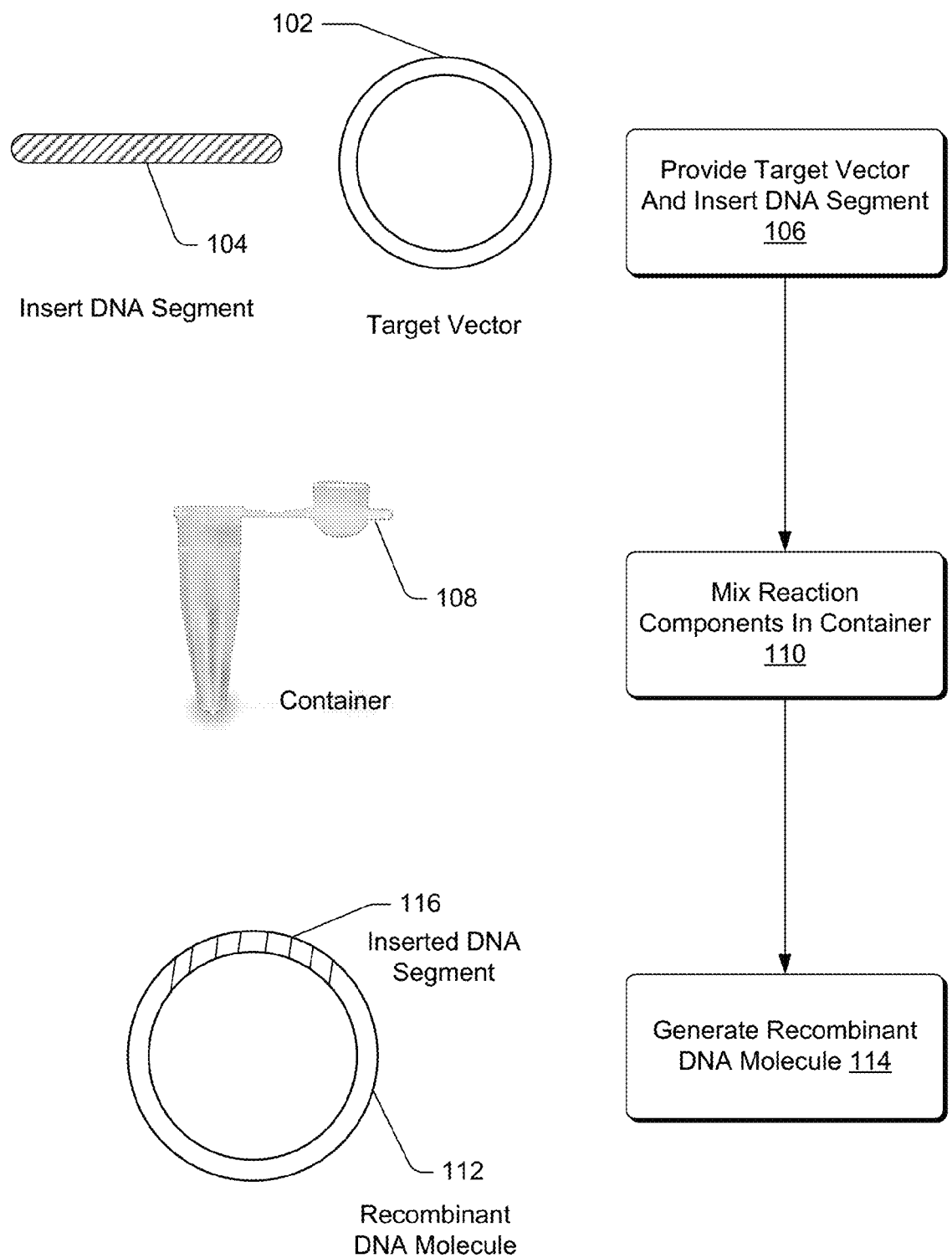
FIG. 1 is a diagram showing an exemplary scheme for directional cloning of an insert DNA segment into a vector.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" is also meant a chemical compounds (e.g., sugars) that has been derived from the basic structure by modification, for example, by conjugation or complexing with other chemical moieties (e.g., glycosylation). The term "derivative" also includes within its scope alterations that have been made to a parent sequence/structure including additions or deletions that provide for functionally equivalent molecules.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, Nucleic Acids Research 12, 387-395) which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The terms "modulating" and "altering" include "increasing" and "enhancing" as well as "decreasing" or "reducing," typically in a statistically significant or a physiologically significant amount or degree relative to a control. In specific embodiments, immunological rejection associated with transplantation of the blood substitutes is decreased relative to an unmodified or differently modified stem cell by at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, or at least 1000%.

An "increased" or "enhanced" amount is typically a "statistically significant" amount, and may include an increase that is 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

A "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein. For example, "In specific embodiments, immunological rejection associated with transplantation of the blood substitutes is decreased relative to an unmodified or differently modified stem cell by at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, or at least 1000%.

By "obtained from" is meant that a sample such as, for example, a polynucleotide or polypeptide is isolated from, or derived from, a particular source, such as a desired organism or a specific tissue within a desired organism. "Obtained from" can also refer to the situation in which a polynucleotide or polypeptide sequence is isolated from, or derived from, a particular organism or tissue within an organism. For example, a polynucleotide sequence encoding a reference polypeptide described herein may be isolated from a variety of prokaryotic or eukaryotic organisms, or from particular tissues or cells within certain eukaryotic organism.

The recitation "polynucleotide" or "nucleic acid" as used herein designates mRNA, RNA, cRNA, rRNA, cDNA or DNA. The term typically refers to polymeric form of nucleotides of at least 10 bases in length, either ribonucleotides or deoxynucleotides or a modified form of either type of nucleotide. For example, polynucleotides may include single and/or double stranded forms of DNA molecules and RNA molecules.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "a polynucleotide having a nucleotide sequence encoding a gene" means a nucleic acid sequence containing the coding region of a gene or in other words the nucleic acid sequence that encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present disclosure may contain endogenous enhancers/promoters, splice junctions, intervening sequences, polyadenylation signals, etc. or a combination of both endogenous and exogenous control elements.

A nucleic acid sequence refers to a series of nucleotides, which is represented by a succession of letters that indicate the order of the nucleotides within a DNA (using G, A, C, and T) or a RNA (using G, A, C, and U) molecule. By convention, a nucleic acid sequence is usually presented from the 5' end to the 3' end. For example, a DNA sequence refers to a series of nucleotides connected one to the other by phosphodiester bonds between the 3' and 5' carbons of adjacent pentoses.

As used herein, the term "recombinant DNA molecule" as used herein refers to a DNA molecule including multiple segments of DNA joined together by means of molecular biological techniques. The term "recombinant protein" or "recombinant polypeptide" as used herein refers to a protein molecule which is expressed from a recombinant DNA molecule.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs that encode these enzymes.

With regard to polynucleotides, the term "exogenous" refers to a polynucleotide sequence that does not naturally-occur in a wild-type cell or organism, but is typically introduced into the cell by molecular biological techniques. Examples of exogenous polynucleotides include vectors, plasmids, and/or man-made nucleic acid constructs encoding a desired protein. With regard to polynucleotides, the term "endogenous" or "native" refers to naturally-occurring polynucleotide sequences that may be found in a given wild-type cell or organism. Also, a particular polynucleotide sequence that is isolated from a first organism and transferred to second organism by molecular biological techniques is typically considered an "exogenous" polynucleotide with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes", which typically catalyze (i.e., increase the rate of) various chemical reactions.

The term "reference sequence" refers generally to a nucleic acid coding sequence, or amino acid sequence, to which another sequence is being compared. All polypeptide and polynucleotide sequences described herein are included as references sequences.

As used herein, the terms "restriction endonucleases" and "restriction enzymes" refer to bacterial enzymes, each of which cut double-stranded DNA at or near a specific nucleotide sequence. For example, an "EcoR" and "BamH" cut a DNA molecule at recognition sites. As used herein, "recognition site" refers to a sequence of specific bases that is recognized by a restriction enzyme if the sequence is present in double-stranded DNA; or, if the sequence is present in single-stranded RNA, the sequence of specific bases that would be recognized by a restriction enzyme if the RNA was reverse transcribed into cDNA and the cDNA employed as a template with a DNA polymerase to generate a double-stranded DNA; or, if the sequence is present in single-stranded DNA, the sequence of specific bases that would be recognized by a restriction enzyme if the single-stranded DNA was employed as a template with a DNA polymerase to generate a double-stranded DNA; or, if the sequence is present in double-stranded RNA, the sequence of specific bases that would be recognized by a restriction enzyme if either strand of RNA was reverse transcribed into cDNA and the cDNA employed as a template with a DNA polymerase to generate a double-stranded DNA. The term "unique restriction enzyme site" indicates that the recognition sequence for a given restriction enzyme appears once within a nucleic acid molecule.

A DNA Ligase refers to an enzyme that creates a phosphodiester bond between the 3' end of one DNA segment and the 5' end of another, while they are base-paired to a template strand. For example, DNA ligase repairs the ends of single-stranded DNA in a duplex DNA chain and/or repair double-strand breaks.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

"Substantially" or "essentially" means nearly totally or completely, for instance, 90%, 95%, 96%, 97%, 98%, 99% or greater of some given quantity.

"Transformation" refers to the permanent, heritable alteration in a cell resulting from the uptake and incorporation of foreign DNA into the host-cell genome; also, the transfer of an exogenous gene from one organism into the genome of another organism.

As used herein, the terms "selectable marker" or "selectable marker gene" refers to the use of a gene which encodes an enzymatic activity that confers the ability to grow in medium lacking what would otherwise be an essential nutrient (e.g., the TRP1 gene in yeast cells); in addition, a selectable marker may confer resistance to an antibiotic or drug upon the cell in which the selectable marker is expressed. A selectable marker may be used to confer a particular phenotype upon a host cell. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene (e.g., the sacB gene which, if expressed, kills the bacterial host cells grown in medium containing 5% sucrose); selectable markers used in this manner are referred to as negative selectable markers or counter-selectable markers.

By "vector" is meant a polynucleotide molecule, preferably a DNA molecule derived, for example, from a plasmid, bacteriophage, yeast or virus, into which a polynucleotide can be inserted or cloned. A vector may contain one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a stem cell. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "PCR product" refers to deoxynucleoside triphosphate(s) copies derived from a DNA template using a polymerase chain reaction (PCR)-based amplification.

Embodiments

Various embodiments relate to methods for directional cloning, which allows an insert DNA to be ligated to a vector in a specific orientation and/or prevent the vector from self-ligation. As defined herein, directional cloning refers to a procedure designed to ensure that an insert DNA is inserted into a target vector molecule in a definite and/or known orientation. The directional cloning may be needed, for example, when the insert DNA is subsequently to be transcribed from a promoter sequence within the target vector.

Under conventional techniques related to the directional cloning, multiple thermal cycles are performed using a PCR machine to generate the desired recombinant target vector. In some instances, sub-cloning is also performed to identify the desired recombined target vector. Embodiments herein related to a surprising or unexpected discovery that cleaving of a target vector and ligating one or more DNA insert DNA segments to the target vector may be performed at substantially the same temperature to form a recombined target vector.

As illustrated in FIG. 1, a method may include providing a target vector 102 and an insert DNA segment 104 at 106. The target vector 102 and the insert DNA segment 104 may be mixed with an amount of a restriction enzyme and an amount of a DNA ligase in a container 108 at 110. In some embodiments, the target vector 102 may be digested and cleaved by the restriction enzyme and at least one portion of the insert DNA segment 104 may be ligated to the cleaved target vector 102 to form a recombinant DNA molecule 112 at 114. In these instances, the at least one portion of the insert DNA segment 104 is represented by an inserted DNA segment 116.

In some embodiments, the recombinant DNA molecule is an expression vector, which may include at least one portion of the target vector and at least one portion of the insert DNA segment.

In some embodiments, the insert DNA segment 104 may include the inserted DNA segment 116 and one or more DNA sequences including recognition sites of the restriction enzyme. For example, the 5' end of the insert DNA segment 104 may include a recognition site of the restriction enzyme such that the recognition site may be removed by the restriction enzyme and the inserted DNA segment 116 may be ligated to the cleaved target vector 102 to form the recombinant DNA molecule 112. In some embodiments, the insert DNA segment 104 may be generated by PCR-based amplification reactions. In some embodiments, the target vector 102 may include recognition sites of the restriction enzyme (e.g., a type II restriction enzyme).

In some embodiments, the target vector 102, the invert DNA segment 104, the restriction enzyme, and the DNA ligase may be mixed in the container 108, for example a microcentrifuge tube. In these instances, the target vector 102 and/or insert DNA segment 104 may be digested and cleaved by the restriction enzyme at a first temperature. The first temperature is the same or substantially the same as a second temperature at which the inserted DNA segment 116 is ligated to the cleaved target vector 102.

In some embodiments, the target vector 102, the invert DNA segment 104, the restriction enzyme, and the DNA ligase may be mixed in the container 108. In these instances, the molecules of the target vector 102 in the container 108 substantially are closed circular plasmids before the molecules of the target vector 102 are digested and cleaved by the restriction enzyme in the container 108. In some embodiments, unlike conventional techniques, the embodiments of the present disclosure may perform the digestion using the restriction enzyme and the ligation using the DNA ligase under the same one or more condition parameters. The condition parameters may include a reaction temperature, a reaction time period, and/or an amount of enzyme usage. For example, the target vector 102, the invert DNA segment 104, the restriction enzyme, and the DNA ligase may be mixed in the container 108 at a room temperature and incubated for 10 minutes, such that the digestion and ligation may be performed under the same condition parameters.

In some embodiments, the target vector 102, the insert DNA segment 104, the amount of the restriction enzyme, and the amount of a DNA ligase may be mixed in the container 108 for a time period of from about 1 minutes to 20 minutes under a temperature of from about 16° C. to about 37° C.

In some embodiments, the restriction enzyme may include a type II restriction enzyme. For example, the type II restriction enzyme may include BsaI, BbsI, BsmBI, Alw26I or LguI. In some embodiments, the DNA ligase may include T4 DNA ligase or E. coli DNA ligase.

In some embodiments, the target vector 102, multiple copies of the insert DNA segment 104, an amount of a restriction enzyme, and an amount of a DNA ligase may be mixed in the container 108 to cleave the target vector 102 and/or the multiple copies of the insert DNA segment 104 at the first temperature, and to ligate multiple copies of at least one portion of the insert DNA segment to the target vector at a second temperature. In some instances, the first temperature is the same or substantially the same as a second temperature.

In some embodiments, the target vector 102, the insert DNA segment 104, an additional insert DNA segment, an amount of a restriction enzyme, and an amount of a DNA ligase may be mixed to cleave the target vector 102, the insert DNA segment 104, and the additional insert DNA segment at a first temperature, and to ligate at least one portion of the insert DNA segment and at least one portion of the additional insert DNA segment to the target vector at a second temperature. In some instances, a sequence of the insert DNA segment 102 may be different from a sequence of the additional insert DNA segment. In some instances, the first temperature is the same or substantially the same as a second temperature

EXAMPLES

Example 1

Preparation of Insert DNA Segments

An insert DNA segment carried a desired insert sequence (SEQ ID NO: 1) and restriction sites (SEQ ID NO: 2) that was recognized by a BsaI restriction enzyme. The restriction sites were located on the 5' and 3' ends of the insert DNA. The insert DNA was amplified by the polymerase chain reaction (PCR). Sequences of the forward and reverse primers designed for the PCR and other sequences are provided in Table 1. Polymerases used in the PCR included Taq or a high fidelity DNA polymerase. After the amplification, the PCR products were purified using enzymes, such as DpnI and/or DMT.

TABLE 1

| Name | Sequence | SEQ ID |
|---|---|---|
| Desired Insert Sequence | CTGACGCCACCATGGTGAGCAAGG GCGAGGAGCTGTTCACCGGGGTGG TGCCCATCCTGGTCGAGCTGGACG GCGACGTAAACGGCCACAAGTTCA GCGTGTCCGGCGAGGGCGAGGGCG ATGCCACCTACGGCAAGCTGACCC TGAAGTTCATCTGCACCACCGGCA AGCTGCCCGTGCCCTGGCCCACCC TCGTGACCACCCTGACCTACGGCG | SEQ ID NO: 1 |

TABLE 1-continued

| Name | Sequence | SEQ ID |
|---|---|---|
| | TGCAGTGCTTCAGCCGCTACCCCG<br>ACCACATGAAGCAGCACGACTTCT<br>TCAAGTCCGCCATGCCCGAAGGCT<br>ACGTCCAGGAGCGCACCATCTTCT<br>TCAAGGACGACGGCAACTACAAGA<br>CCCGCGCCGAGGTGAAGTTCGAGG<br>GCGACACCCTGGTGAACCGCATCG<br>AGCTGAAGGGCATCGACTTCAAGG<br>AGGACGGCAACATCCTGGGGCACA<br>AGCTGGAGTACAACTACAACAGCC<br>ACAACGTCTATATCATGGCCGACA<br>AGCAGAAGAACGGCATCAAGGTGA<br>ACTTCAAGATCCGCCACAACATCG<br>AGGACGGCAGCGTGCAGCTCGCCG<br>ACCACTACCAGCAGAACACCCCCA<br>TCGGCGACGGCCCCGTGCTGCTGC<br>CCGACAACCACTACCTGAGCACCC<br>AGTCCGCCCTGAGCAAAGACCCCA<br>ACGAGAAGCGCGATCACATGGTCC<br>TGCTGGAGTTCGTGACCGCCGCCG<br>GGATCACTCTCGGCATGGACGAG<br>CTGTACAAGTAA | |
| Restriction Site | GGTCTCN'NNNN | SEQ ID NO: 2 |
| Forward Primer | GGGGggtctcttgacGCCAC CATGGTGAGCAAGG | SEQ ID NO: 3 |
| Reverse Primer | GCCGggtctcggagtTGGTC TCGGAGTTTACTTGTACAG CTCGTCCATGCC | SEQ ID NO: 4 |

Example 2

Figure 2:
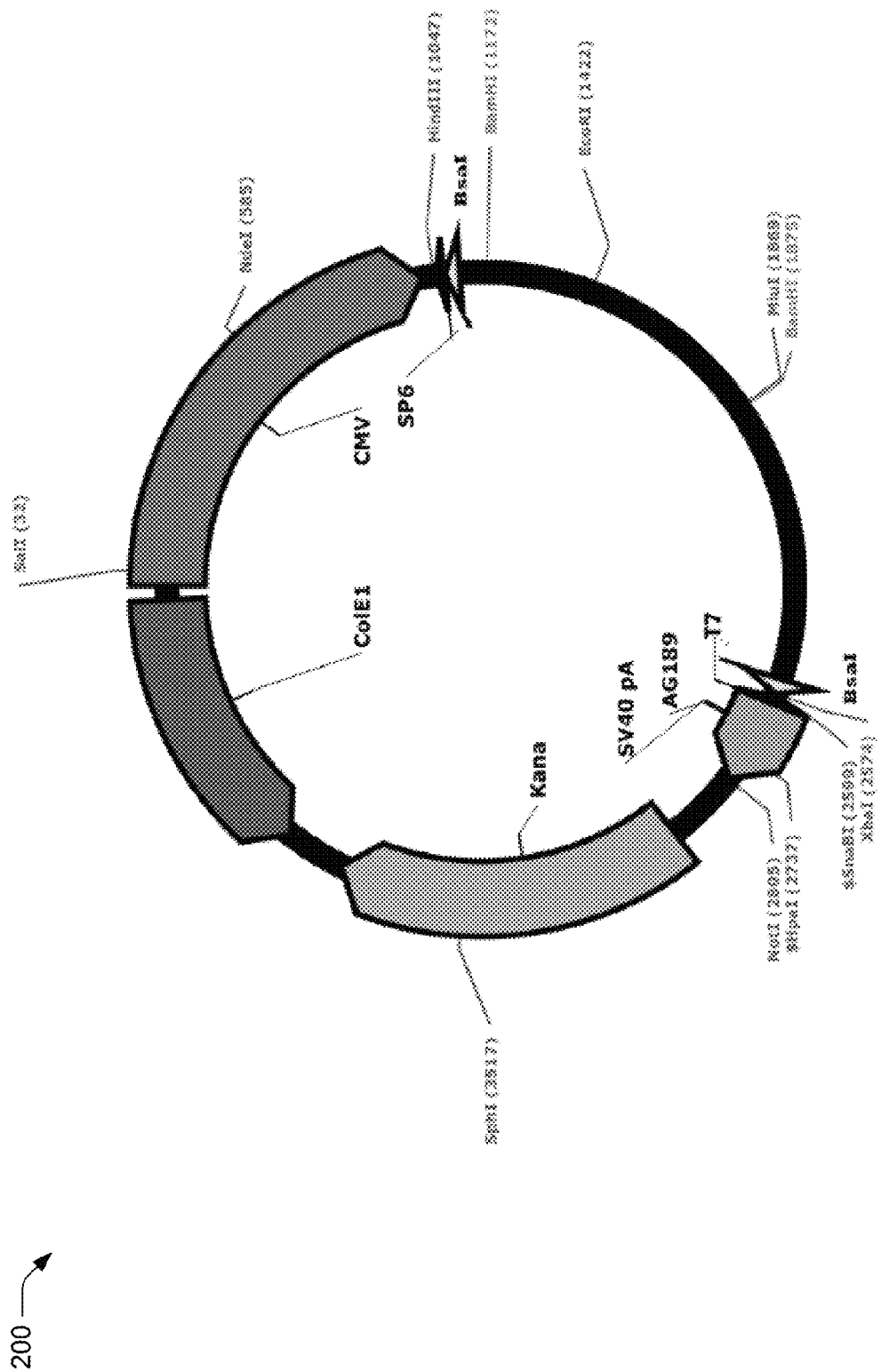
FIG. 2 is a diagram showing an exemplary plasmid.

Generation of Expression Vectors 1-50 nanogram (ng) of the purified insert DNA segments were mixed with 25 ng of pSDS201 plasmid, 10× buffer, an enzyme mixture including 20 U restriction enzyme and 5 U T4 DNA ligase (e.g., 1 ul restriction enzyme and 1 ul T4 DNA ligase), and double-distilled water (ddH2O) in a single tube. More detailed information is presented in Table 2. The pSDS201 plasmid is about 4600 bp and includes multiple restriction sites of BsaI. As shown in FIG. 2, construct 200 illustrates construct of a pSDS201 plasmid. The mixture was incubated at a temperature of from 22° C. to 37° C. for 10 minutes to obtained reaction products including recombed DNA molecules. An individual recombined DNA molecule of the recombined DNA molecules include the desired insert sequence and the plasmid.

TABLE 2

| Components | Volume |
|---|---|
| Plasmids | 25 ng |
| Inserts | 1-50 ng |
| 10x Buffer | 2 μl |
| Enzyme Mix | 2 μl |
| ddH$_2$O | Up to 20 μl |
| Total | 20 μl |

Example 3

Transformation and Assay of the Expression Vectors

After the incubation, 10 μl of the reaction products were mixed with 100 μl solution containing $10^8$ units of DH5α competent cells to obtain various transformants. These transformants were first screened based on a selectable marker (e.g., Kana) in the pSDS201 plasmids. Colony screening methods were further performed to select the transformant including expression vectors containing the recombined DNA molecules. The colony screening methods included colony PCR, restriction endonuclease digestion, and/or DNA sequencing.

What is claimed is:

1. A method for directional cloning, the method comprising the following steps in the order named:
   (1) providing a closed circular plasmid, a double-stranded linearized polynucleotide, an amount of a restriction enzyme, and an amount of a DNA ligase;
   (2) incubating the closed circular plasmid, the double-stranded linearized polynucleotide, the amount of the restriction enzyme, and the amount of the DNA ligase in a single container at about 37° C. for about 10 minutes, thereby cleaving the closed circular plasmid with the restriction enzyme, ligating at least one portion of the double-stranded linearized polynucleotide to the cleaved closed circular plasmid to generate a recombinant DNA molecule comprising at least one portion of the closed circular plasmid and at least one portion of the double-stranded linearized polynucleotide, thus obtaining a mixture comprising the recombinant DNA molecule; and
   (3) mixing a portion of the mixture with competent host cells about 10 minutes after starting the incubation of step (2), wherein:
   the restriction enzyme is at a concentration of about 20 units in a volume of 20 μl of the mixture, the restriction enzyme comprises at least one of BsaI, BbsI, BsmBI, Alw26I or LguI, and
   the DNA ligase is at a concentration of about 5 units in a volume of 20 μl of the mixture.

2. The method of claim 1, wherein the recombinant DNA molecule is an expression vector.

3. The method of claim 1, wherein the double stranded linearized polynucleotide comprises DNA sequences comprising recognition sites of the restriction enzyme.

4. The method of claim 1, wherein the DNA ligase comprises at least one of T4 DNA ligase or *E. coli* DNA ligase.

5. The method of claim 1, wherein the double stranded linearized polynucleotide is a polymerase chain reaction (PCR) product.

6. The method of claim 1, wherein the double-stranded linearized polynucleotide is about 700 bp to 800 bp.

* * * * *